(12) United States Patent
Regelman (10) Patent No.: US 10,048,198 B2
(45) Date of Patent: Aug. 14, 2018

(54) METHOD AND SYSTEM FOR OPTICAL MEASUREMENTS OF CONTAINED LIQUIDS HAVING A FREE SURFACE

(71) Applicant: BacterioScan Inc., St. Louis, MO (US)

(72) Inventor: Dan Vadim Regelman, Kiryat Bialik (IL)

(73) Assignee: BacterioScan Ltd., MP Western Galilee (IL)

( * ) Notice: Subject to any disclaimer, the term of this patent is extended or adjusted under 35 U.S.C. 154(b) by 315 days.

(21) Appl. No.: 14/559,286

(22) Filed: Dec. 3, 2014

(65) Prior Publication Data

US 2015/0160118 A1 Jun. 11, 2015

Related U.S. Application Data

(60) Provisional application No. 61/912,753, filed on Dec. 6, 2013.

(51) Int. Cl.
| | | |
|---|---|---|
| *G01N 21/51* | (2006.01) | |
| *E21B 47/10* | (2012.01) | |
| *G01N 21/64* | (2006.01) | |
| *G01N 21/03* | (2006.01) | |

(52) U.S. Cl.
CPC .......... *G01N 21/51* (2013.01); *E21B 47/102* (2013.01); *G01N 21/645* (2013.01); *G01N 21/0303* (2013.01); *G01N 21/6452* (2013.01); *G01N 2021/6478* (2013.01)

(58) Field of Classification Search
None
See application file for complete search history.

(56) References Cited

U.S. PATENT DOCUMENTS

| | | |
|---|---|---|
| 3,627,424 A | 12/1971 | Dorman et al. |
| 3,713,775 A | 1/1973 | Schmitz |
| 3,832,532 A | 8/1974 | Praglin et al. |
| (Continued) | | |

FOREIGN PATENT DOCUMENTS

| | | |
|---|---|---|
| DE | 10128978 | 12/2002 |
| EP | 0320154 | 6/1989 |
| (Continued) | | |

OTHER PUBLICATIONS

Murray, et al. "Light-scattering methods for antibiotic sensitivity tests", J Clin Pathol, 1980, vol. 33, pp. 995-1001, 8 pages.
(Continued)

*Primary Examiner* — Jill Culler
(74) *Attorney, Agent, or Firm* — Nixon Peabody LLP (57) ABSTRACT

The present invention is an optical measurement system for measuring a liquid sample within a well. The system comprises a light source configured to transmit light though the well, a detector configured to measure optical signals derived from the transmitted light, and a tunable optical element. The tunable optical element is positioned between the light source and the well. The tunable optical element is operable to shape the light to compensate for distortions induced by a surface of the liquid sample. The detector is preferably located below the well for receiving a forward scatter signal indicative of at least one characteristic of the particles within the liquid sample.

19 Claims, 5 Drawing Sheets

(56) References Cited

U.S. PATENT DOCUMENTS

| | | | |
|---|---|---|---|
| 3,928,140 A | 12/1975 | Wyatt et al. | |
| 4,066,360 A | 1/1978 | Breddin et al. | |
| 4,101,383 A | 7/1978 | Wyatt et al. | |
| 4,113,386 A | 9/1978 | Lepper, Jr. | |
| 4,119,407 A | 10/1978 | Goldstein et al. | |
| 4,265,538 A | 5/1981 | Wertheimer | |
| 4,431,307 A * | 2/1984 | Suovaniemi | G01N 21/03 |
| | | | 356/246 |
| 4,577,970 A | 3/1986 | Meserol | |
| 4,754,613 A | 7/1988 | Brito | |
| 4,874,102 A | 10/1989 | Jessop | |
| 4,895,446 A | 1/1990 | Maldari et al. | |
| 5,077,481 A * | 12/1991 | Hoult | G01N 21/8507 |
| | | | 250/576 |
| 5,082,628 A * | 1/1992 | Andreotti | G01N 21/76 |
| | | | 250/361 C |
| 5,139,031 A | 8/1992 | Guirguis | |
| 5,187,368 A | 2/1993 | Galante et al. | |
| 5,212,667 A | 5/1993 | Tomlinson, Jr. et al. | |
| 5,351,118 A | 9/1994 | Spinell | |
| 5,616,923 A | 4/1997 | Rich et al. | |
| 5,693,944 A | 12/1997 | Rich | |
| 5,969,814 A | 10/1999 | Barber | |
| 5,989,499 A | 11/1999 | Catanzariti | |
| 6,091,483 A | 7/2000 | Guirguis | |
| 6,159,686 A * | 12/2000 | Kardos | G01N 33/588 |
| | | | 250/484.2 |
| 6,230,045 B1 | 5/2001 | Hoogenraad et al. | |
| 6,333,008 B1 | 12/2001 | Leistner et al. | |
| 6,573,992 B1 | 6/2003 | Drake | |
| 6,673,532 B2 * | 1/2004 | Rao | C12M 23/12 |
| | | | 435/287.1 |
| 6,861,230 B1 | 3/2005 | Murphy et al. | |
| 7,430,046 B2 | 9/2008 | Jiang et al. | |
| 7,961,311 B2 | 6/2011 | Weichselbaum et al. | |
| 8,339,601 B2 | 12/2012 | Weichselbaum et al. | |
| 8,531,676 B2 * | 9/2013 | Condit | A61B 5/0066 |
| | | | 356/479 |
| 2003/0048433 A1 | 3/2003 | Desjonqueres | |
| 2004/0070756 A1 | 4/2004 | Rastopov | |
| 2004/0185552 A1 | 9/2004 | Grinner et al. | |
| 2004/0238746 A1 | 12/2004 | Dreyer et al. | |
| 2005/0148085 A1 | 7/2005 | Larsen | |
| 2006/0063146 A1 | 3/2006 | Larsen et al. | |
| 2006/0109476 A1 | 5/2006 | Werner et al. | |
| 2006/0256338 A1 | 11/2006 | Gratton et al. | |
| 2007/0155017 A1 | 7/2007 | Wyatt | |
| 2007/0159619 A1 | 7/2007 | Chu et al. | |
| 2007/0195324 A1 | 8/2007 | Adams et al. | |
| 2007/0206203 A1 | 9/2007 | Trainer | |
| 2007/0211251 A1 | 9/2007 | Weichselbaum | |
| 2007/0253042 A1 | 11/2007 | Szarvas | |
| 2008/0106737 A1 | 5/2008 | Weichselbaum et al. | |
| 2008/0293091 A1 | 11/2008 | Kanipayor | |
| 2010/0264295 A1 * | 10/2010 | Van Dijk | 250/201.4 |
| 2010/0277734 A1 | 11/2010 | Weichselbaum | |
| 2013/0089476 A1 | 4/2013 | Weichselbaum et al. | |
| 2014/0322729 A1 * | 10/2014 | Fan | G01N 21/31 |
| | | | 435/7.9 |

FOREIGN PATENT DOCUMENTS

| | | |
|---|---|---|
| EP | 1136563 | 9/2001 |
| GB | 1515681 | 6/1978 |
| GB | 2412166 | 9/2005 |
| WO | WO 00/09981 | 2/2000 |
| WO | WO 00/66763 | 11/2000 |
| WO | WO 2006/018839 | 2/2006 |
| WO | WO 2013/070948 A1 | 5/2013 |
| WO | WO 2013/153371 A1 | 10/2013 |

OTHER PUBLICATIONS

PCT International Search Report and Written Opinion of the International Search Authority regarding PCT/IL2006/01379, dated Jul. 11, 2008, 8 pages.

International Search Report, PCT/US14/68389, 2 pages, dated Mar. 5, 2015.

International Written Opinion, PCT/US14/68389, 6 pages, dated Mar. 5, 2015.

* cited by examiner

METHOD AND SYSTEM FOR OPTICAL MEASUREMENTS OF CONTAINED LIQUIDS HAVING A FREE SURFACE

RELATED APPLICATIONS

The present application claims priority to U.S. Provisional Application Ser. No. 61/912,753, filed Dec. 6, 2013, titled "Method and System for Optical Measurements of Contained Liquids with the Free Surfaces," which is herein incorporated by reference in entirety.

COPYRIGHT

A portion of the disclosure of this patent document may contain material which is subject to copyright protection. The copyright owner has no objection to the facsimile reproduction by anyone of the patent disclosure, as it appears in the Patent and Trademark Office patent files or records, but otherwise reserves all copyright rights whatsoever.

FIELD OF THE INVENTION

The present invention relates generally to the field of optical measurements of contained liquid samples. Specifically, the present invention relates to a system having a tunable optical element for obtaining high-sensitivity optical measurements from a liquid having a free surface that may have distortions, such as a meniscus. Such a system may perform multiple optical measurements on samples contained in a two dimensional array of wells within a microplate.

BACKGROUND OF THE INVENTION

Many applications in the field of analytical research and clinical testing utilize optical methods for analyzing liquid samples. Among those methods are absorbance, turbidity, fluorescence/luminescence, and optical scattering measurements. Optical laser scattering is one of the most sensitive methods, but its implementation can be very challenging, especially when analyzing biological samples in which suspended particles are relatively transparent in the medium. In this case, most of the scattering process occurs in the forward direction near the incident laser beam. To detect this low-angle, forward scattering signal, high extinction of the incident beam is required. But various optical effects (e.g., such as laser beam spatial purity, optical surface scattering, and beam distortions by the free liquid surface) often interfere with the extinction of the incident beam. For this reason, the forward scattering method is rarely applied in spite of its sensitivity.

In the case of fluorescence/luminescence detection, there is a spectral separation between the excitation light and the emitted light, which can help to facilitate the extinction of the excitation light by means of spectroscopic techniques, such as notches, bandpass optical filters, or monochromators. But in many application cases, the fluorescence signal is many orders of magnitude lower compared to the excitation light intensity and the excitation-light extinction by wavelength separation is not sufficient. For this reason, many systems collect the emitted light from a direction that is opposite of or normal to the excitation beam, such that the excitation light does not reach the detector. However, this can results in a rather complex optical layout, sometimes utilizing multiple detectors.

One particularly important application of optical measurements of liquid samples involves a microplate reader used for microbiologic assays. A microplate comprises of multiple open-top wells containing individual samples arranged in a two dimensional array (e.g., 8×12). To obtain useful information on the samples content, the microplate reader may utilize one or more types of optical measurements. Because of a two dimensional arrangement, the optical access is typically available in only the top and bottom directions of the wells. The upper free surface of the liquid sample is normally curved due to the liquid's surface tension. This curvature combined with the relatively small diameter of the wells cause a significant incident beam divergence or distortion, making its extinction very difficult and inefficient before it reaches the detector. This is one reason that forward scatter signal measurement or a fluorescence signal measurement in the input-beam direction is not easily implemented in wells of a microplate.

Accordingly, there is a need for an improved optical measurement system that allows for the detection of the forward scatter signals and/or forward fluorescence signals in the input-beam direction so as to allow for a determination of the size, quantity, and/or concentration of particles (e.g., bacteria) in the liquid.

SUMMARY OF THE INVENTION

In one aspect, the present invention involves a method for overcoming the aforementioned problems by generating an input beam with a controlled distortion, and correcting the distortion induced by a free-liquid surface. As such, the method includes a substantially collimated or focused beam at the detector, while separating the desired scattering signals and/or fluorescence signals by efficiently blocking the input beam from detection.

In another aspect, the present invention involves an apparatus or system equipped with a single detector array, for high sensitivity scattering measurements at several scattering angles. The detector may receive back scatter signals, low-angle forward scatter signals, fluorescence signals, and absorbance measurement signals, all using a single detector array In yet a further aspect, the present invention is an optical measurement system for measuring a liquid sample. The system comprises a light source configured to transmit light though the well, a detector configured to measure optical signals derived from the transmitted light, and a tunable optical element. The tunable optical element is positioned between the light source and the well. The tunable optical element is operable to shape the light to compensate for distortions induced by a surface of the liquid sample.

The present invention is also a method of determining at least one characteristic of particles within a liquid that is contained in a well. The method includes transmitting a light beam toward a free surface of the liquid and, prior to the light beam impinging on the free surface, altering a shape of the light beam to result in a substantially collimated or focused beam within the liquid after the input beam has been subjected to optical distortions at the free surface. The method further includes attenuating the input beam at a location outside of the well and before a detector, and receiving forward scatter signals at the detector. The forward scatter signals are indicative of at least one characteristic of the particles.

In yet a further embodiment, the present invention is an optical measurement system for measuring at least one characteristic of particles within a liquid that is contained in a well. The system comprises a light source, a tunable optical element, a detector, and an input-beam attenuator. The light source is for transmitting an input beam toward a free surface(s) of the liquid and in a manner that is generally parallel to a central axis of the well. The tunable optical element is located between the light source and the free surface(s) of the liquid. The tunable optical element is for altering the shape of the input beam to compensate for a distortion associated with the free surface(s) of the liquid. The detector is located below the well for receiving a forward scatter signal indicative of at least one characteristic of the particles within the liquid. The input-beam attenuator is for inhibiting a transmitted portion of the input beam from impinging upon the detector. The transmitted portion of the input beam is the portion of the input beam that has transmitted through the liquid.

Additional aspects of the invention will be apparent to those of ordinary skill in the art in view of the detailed description of various embodiments, which is made with reference to the drawings, a brief description of which is provided below.

While the invention is susceptible to various modifications and alternative forms, specific embodiments will be shown by way of example in the drawings and will be described in detail herein. It should be understood, however, that the invention is not intended to be limited to the particular forms disclosed. Rather, the invention is to cover all modifications, equivalents, and alternatives falling within the spirit and scope of the invention as defined by the appended claims.

DETAILED DESCRIPTION

The drawings will herein be described in detail with the understanding that the present disclosure is to be considered as an exemplification of the principles of the invention and is not intended to limit the broad aspect of the invention to the embodiments illustrated. For purposes of the present detailed description, the singular includes the plural and vice versa (unless specifically disclaimed); the words "and" and "or" shall be both conjunctive and disjunctive; the word "all" means "any and all"; the word "any" means "any and all"; and the word "including" means "including without limitation."

Figure 1:
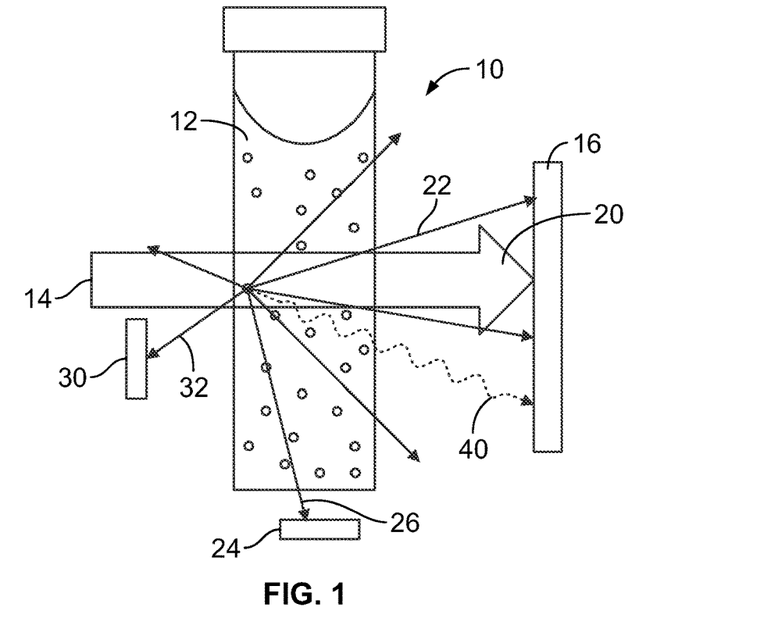
FIG. 1 schematically illustrates the various types of optical measurements, each of which is individually known to be in the prior art, that may result from an input beam passing through a liquid in a direction transverse to the container's primary axis.

FIG. 1 schematically illustrates the various optical measurements that may be taken on a vial 10 containing a liquid 12 having suspended particles (e.g., bacteria). The incident input beam 14 (also called an "excitation" beam in the case of fluorescence/luminescence) passes through the liquid 12 and interacts with the suspended particles. As one example, the input beam 14 may be derived from an LED.

The various types of optical measurements in FIG. 1 are individually known in the prior art. A first detector 16 is located on the opposite side of the input beam 14. The input beam 14 is partially absorbed within the liquid 12 such that an output beam 20 is received by the first detector 16 and is indicative of the absorbance of the particle-filled liquid 12. Additionally, the receiver 16 can detect a scatter signal 22 resulting from the input beam 14 scattering from the various particles within the liquid 12. Additionally, a second receiver 24 measures a high-angle side scatter signal 26 in a direction that is generally perpendicular to the input beam 14. And a third receiver 30 measures the back scatter signal 32 caused by energy reflecting from the particles in a direction generally opposite to the input beam 14. Finally, a portion of the input beam 14 is absorbed by particles, which is then re-emitted at a wavelength that is characteristic to the particle molecular structure. The process is known as fluorescence, which is a type of photo-luminescence. This fluorescence signal 40 is generally emitted in all directions, and can be picked up by all the detectors sensitive in the spectral range of the emitted radiation. It should be noted that FIG. 1 is for the purpose of illustrating the individual types of signals that are detectable when an input beam is passed through a liquid. While these types of signal detectors are available individually within the prior art, all of their combinations are not, however, necessarily a part of the state of the prior art.

In summary, there are several types of optical measurements available when the input beam 14 is transmitted into the liquid 12 containing particles. The first type of optical measurement detects the fluorescence signals 40, which is generally emitted in all directions and can be emitted at multiple wavelengths. The second type of optical measurement detects absorbance, which is performed by evaluating the intensity of the output light beam 20 that has passed through the liquid 12. The third type of optical measurement involves light that is elastically scattered by the particles in the liquid 12 in various directions. As such, the input beam can be both absorbed and scattered by the suspended particles, both of which prevent the incident input beam from reaching the first detector 16. The amount of absorbed and scattered light is related to the characteristics of the particles, such as particle concentration and can be determined through known special calibration techniques. When the particles are bacteria, they can be detected and counted by various techniques, which are generally described in U.S. Pat. Nos. 7,961,311 and 8,339,601, both of which are commonly owned and are herein incorporated by reference in their entireties.

Regarding this third type of optical measurement involving scattering, there are three major types of scattering signals—back scatter signals 32, forward scatter signals 22, and side scatter signals 26. Detection of side scatter signals 26 is also known as nephelometry, which evaluates a parameter (sometimes called "turbidity") that, in certain cases, can be also be linked directly by calibration to particle concentration.

Figure 2A:
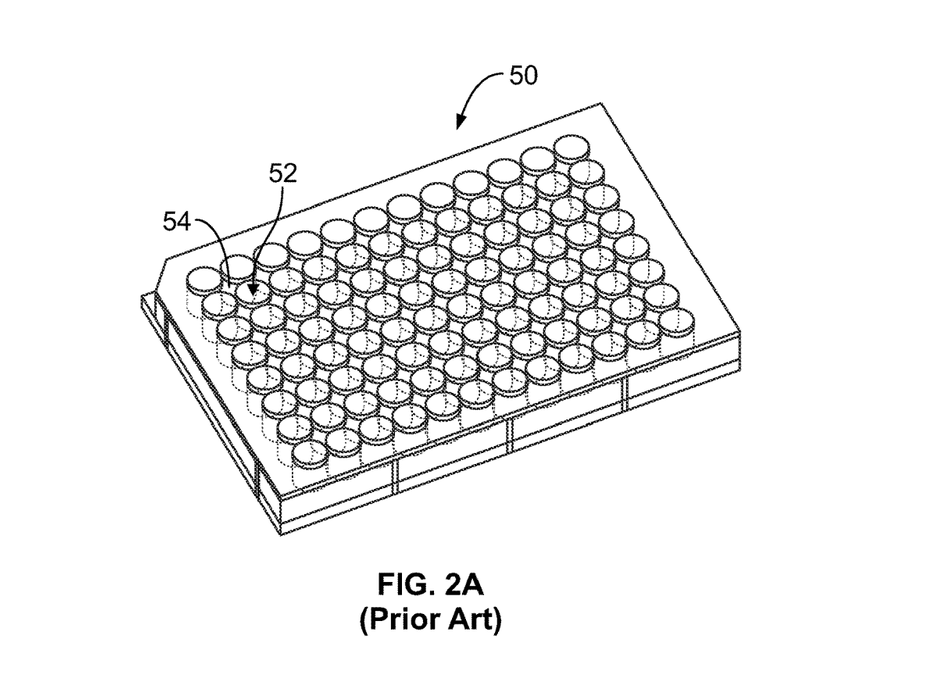
FIG. 2A is a perspective view of a microplate containing a plurality of wells that containing liquid samples.

FIG. 2A illustrates a common microplate 50 having a two-dimensional array of wells 52 extending downwardly from a top surface 54. Each of the wells 52 typically has an elongated shape and contains a liquid sample for measurement. However, optical access for all of the wells 52 is possible only from the top and the bottom of the microplate 50, while optical access from the side is very limited for the interior wells 52.

Figure 2B:
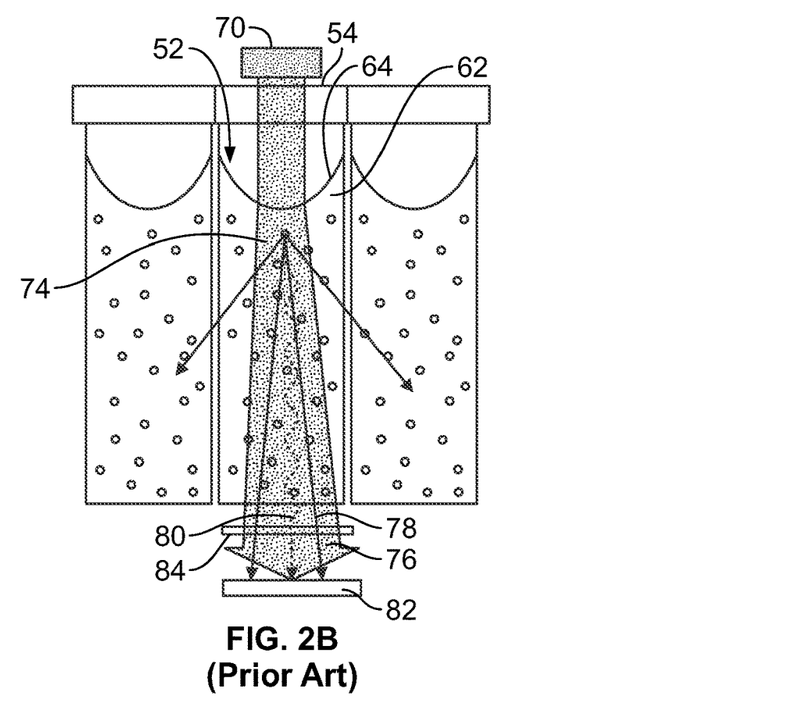
FIG. 2B is a schematic illustration of a system for taking an optical measurement of a liquid along the primary axis of one of the wells of the microplate in FIG. 2A.

FIG. 2B illustrates a typical layout for optical measurements detected from a liquid 62 within one of the wells 52 of the microplate 50. The liquid 62 has a free surface 64 that is characterized by a meniscus due to the surface tension of the liquid 62. A laser 70 provides an input beam 74 that enters the liquid 62 from above the top surface 54 of the microplate and is detected from the bottom. In particular, the input beam 74 results in an output beam 76, a forward scatter signal 78, and a fluorescence signal 80 that are transmitted towards a detector 82.

If the fluorescence signal 80 is to be measured, an optical filter or a monochromator 84 is utilized to remove the incident output beam 76 before it reaches the detector 82. But for either an optical filter or a monochromator 84, the ability to discriminate the wavelength of the incident output beam 76 from the fluorescence signal 80 is limited by the filter's rejection ability or the monochromator's quality, which is typically on the order $10^{-5}$ to $10^{-8}$, respectively. But in many cases, the fluorescence signal 80 is weak, or the particle concentration in the liquid 62 is low, thereby requiring extremely low fluorescence signals 80 to be measured. And for those cases, a higher rejection ratio should be implemented, such that physical blocking of the incident output beam 76 is required, which is problematic because it limits the ability to also detect the fluorescence signal 80 from the bottom. As will be described in more detail, the present invention resolves this problem with the fluorescence signal 80 because the incident beam is blocked, leaving the fluorescence signal 80 (perhaps filtered through a filter) as the primary signal received at the detector.

The liquid 62 contained in the microplate well 54 typically has a highly curved free surface 64 due to surface tension. This free surface 64 has an optical power (sometimes with a significant optical aberration), substantially distorting the input beam 74 and causing it to diverge as shown in FIG. 2B. Because of this effect on the input beam 74, blocking the output beam 76 or detecting the front-scatter signal 78 at low angles is impossible. Accordingly, the only practical optical measurements that are left in place are detection of the absorbance, the back scatter signal, and backward-emitted fluorescence. If absorbance is measured, there is no need for the optical filter or a monochromator 84 in FIG. 2B. In summary, the divergence of the input beam 74 caused by the liquid's free surface 64 negates the ability to effectively shield or filter the detector 82 from the output beam 76, thereby inhibiting the detection of the forward-emitted fluorescence 80 or the forward scatter signal 78, leaving only absorbance to be detected from the bottom of the microplate 50. The present invention, which is generally described in FIG. 3, helps to resolve this problem by correcting the distortions caused by the free surface 64.

Figure 3:
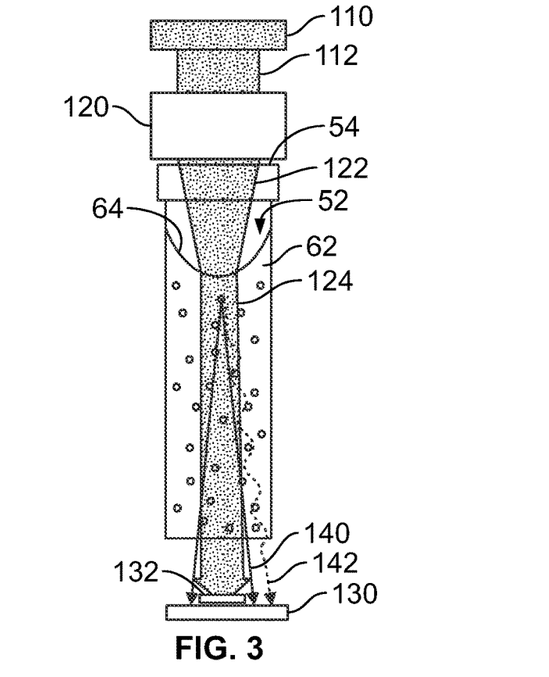
FIG. 3 is a schematic view of the optical measurement system with a tunable optical element in accordance with the present invention.

FIG. 3 illustrates one embodiment of the present invention that permits the detection of the forward scatter signal as well as the forward emitted fluorescence. Specifically, the system includes a laser 110 as an optical source that produces an input beam 112 generally parallel to the central axis of the well 52. In one preferred embodiment, the input beam 112 of the laser 110 is in a wavelength in the visible to near infrared (e.g., 300 nm to 2500 nm) and has a power in the range from about 0.10 milliwatts to 10 milliwatts. The input beam 112 is shaped by a tunable output element 120 located above the top surface 54 of the microplate 50. The tunable output element 120 creates a specifically shaped converging input beam 122 that enters the liquid 62 from the free surface 64. Notably, the tunable output element 120 achieves a certain convergence that negates the distorting effect caused by the meniscus at the free surface 64, thereby resulting in a substantially collimated beam 124 (or a focused beam) that travels through the liquid 62 within the well 52 of the microplate 50 toward a detector 130. In one particular embodiment, the tunable output element 120 can be adjusted in the range from −10 and +30 dpt for a well 52 with a 6.7 mm diameter. The collimated beam 124 is acted upon by a beam dump 132 (or other type of attenuator) after leaving the well 154, but before reaching the detector 130. In this case, the collimated beam 124 can be physically blocked by the beam dump 132, enabling measurement of the low-angle forward scatter signal 140 and/or the fluorescence signal 142 with a high extinction ratio relative to the collimated beam 124. As such, the limited geometric area of the collimated beam 124 can be controlled, such that the detector 130 receives substantially only the forward scatter signal 140 and/or the fluorescence signal 142.

When implementing an optical measurement system according to the schematic illustration of FIG. 3, it may be useful to include additional optical components. For example, a pinhole aperture (e.g., 0.5 mm pinhole) can be placed adjacent to the laser 110 to limit the output beam 112 to a specific size and shape. Similarly, the pinhole aperture (e.g., 0.1 mm to 1.0 mm pinhole) can also be placed below the tunable output element 120 and above the upper surface 54 the microplate 150 to help limit the light energy passed into the free surface 64 of the liquid 62.

Figure 4A:
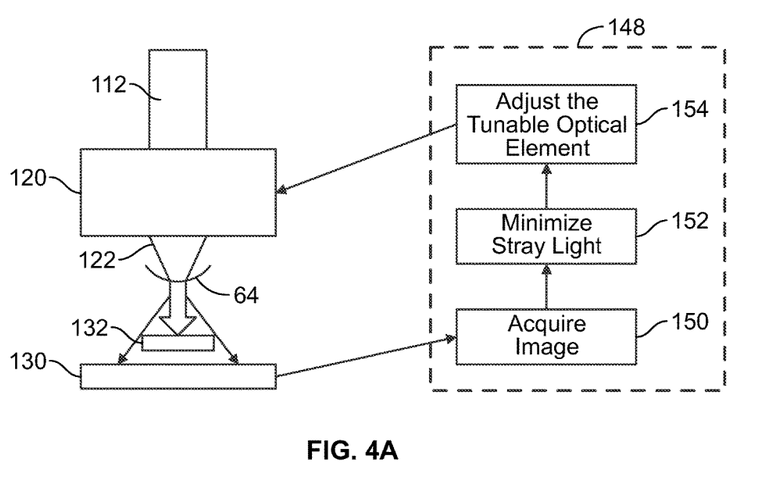
FIG. 4A illustrates one method for adjusting the tunable optical element in the system of FIG. 3.
Figure 4B:
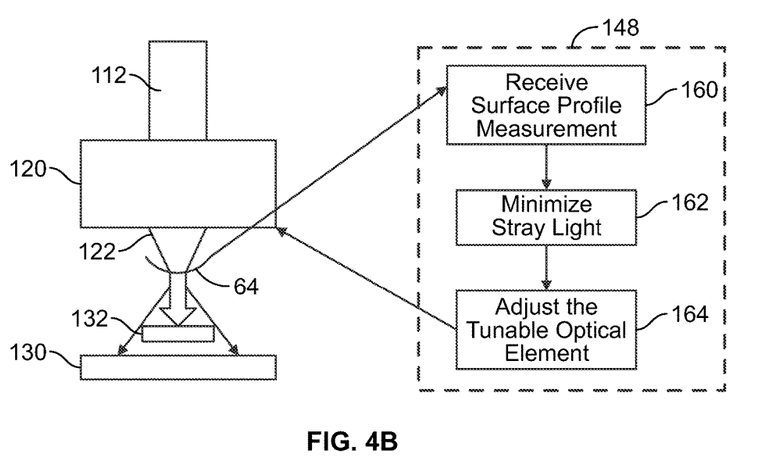
FIG. 4B illustrates another method for adjusting the tunable optical element in the system of FIG. 3.

FIGS. 4A and 4B illustrate feedback loops for the tunable output element 120 illustrated in FIG. 3. In FIG. 4A, the detector 130 acquires the signal from the collimated beam 124 after being acted upon (likely partially) by the beam dump 132. The characteristics of the optical signal from the collimated beam 124 are received by a controller 148 that executes an image acquisition algorithm at step 150 to extract data corresponding to the position, the dimension, and the intensity of the collimated beam 124 that are received on the image plane of the detector 130. These optical signals received by the detector 130 can be considered as stray light. Based on the known characteristics of the focused convergent beam 122 before entering the free surface 64 of the liquid 62, and the data corresponding to the position, dimension, and intensity distribution on the detector 130, a physical profile of the free surface 64 is calculated or approximated. In other words, the optical characteristics of the free surface 64 are now known, as if it were a lens. The controller 148 executes a stray-light minimization algorithm at step 152 that calculates the wavefront compensation to be introduced into the input beam 112 by the tunable optical element 120 to minimize the beam distortion caused by the free surface 64 of the liquid 62, thereby achieving the collimated beam 124. The controller 148 then adjusts the tunable optical element 120 at step 154, thereby altering the optical settings of the tunable optical element 120. The process may continue periodically, or iteratively, until the desired collimated beam 124 is produced, thereby creating a minimum amount of stray light on the detector 130. When achieved, the system can operate at a more optimum state for receiving the forward scatter signal 140 and/or the fluorescence signal 142, as shown in FIG. 3.

In the feedback loop of FIG. 4B, the detector 130 is not used as part of the feedback loop. Rather, the free surface 64 of the liquid is measured directly or indirectly in other ways, such as a mechanical measurement, optical power measurement, or calculations based on knowing surface tension parameters. The determined profile of the free surface 64 is used by the controller 148 to determine the optimal settings for the tunable optical element 120. Accordingly, the controller 148 receives data at step 160 to determine the surface profile of the free surface 64 (e.g., measures reflections from the free surface 64). The controller 148 executes a stray-light minimization algorithm at step 162 that calculates the wavefront compensation to be introduced into the input beam 112 by the tunable optical element 120 to minimize the beam distortion caused by the free surface 64 of the liquid 62 and achieve the collimated beam 124. The controller 148 then adjusts the tunable optical element 120 at step 164 to alter the optical settings of the tunable optical element 120. The process continues periodically, or iteratively, until identifying the desired convergent beam 122 that exits the tunable optical element 120 will result in the desired collimated beam 124.

Figure 5A:
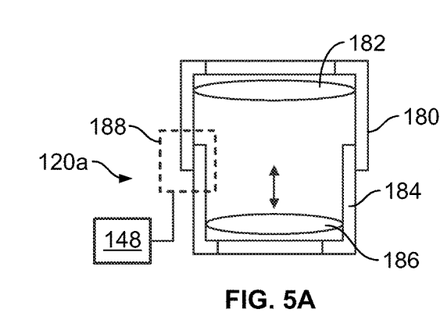
FIG. 5A illustrates one type of tunable optical element involving a mechanically adjustable optical element.
Figure 5B:
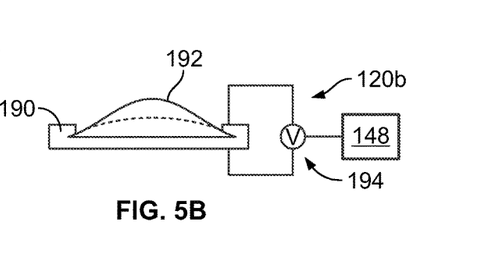
FIG. 5B illustrates a second type of tunable optical element involving an electronically or mechanically tunable lens.
Figure 5C:
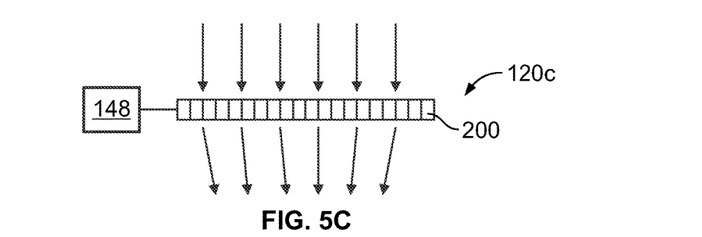
FIG. 5C illustrates a third type of tunable optical element involving a spatial light modulator.

FIGS. 5A-5C illustrate exemplary implementations of the tunable optical element 120. In FIG. 5A, the tunable optical element 120a is a mechanically adjustable assembly comprising a first structure 180 attached to first optical element 182 (such as a lens) and a second structure 182 attached to a second optical element 184. In response to control signals received from the controller 148, an actuator 188 (such as a motor) imparts a force on the first structure 180 and/or the second structure 184 to adjust the distances between the first optical element 182 and the second optical element 184. The adjustment of the distances between the first optical element 182 and the second optical element 184 affects the shape of the convergent beam 122 (FIG. 3) that exits the tunable optical element 120a.

In FIG. 5B, the tunable optical element 120b includes a mounting structure 190 that holds a mechanically or electronically tunable lens 192. The controller 148 adjusts the electrical output of a circuit 194 that directly affects the shape of the electronically tunable lens 192. Alternatively, the controller 148 adjusts the output of the circuit 194 to alter the shape of the mechanical mounting structure 190, thereby indirectly affecting the shape of the tunable lens 192. The adjustment of the shape of the tunable lens 192 affects the shape of the convergent beam 122 (FIG. 3) that exits the tunable optical element 120b.

In FIG. 5C, the tunable optical element 120c includes a spatial light modulator (SLM) 200. The controller 148 adjusts the SLM 200 to provide a great amount of control of the beam 122 that transmits through the free surface 64. The SLM 200 may compensate for virtually any surface distortion free surface 64, but at a limited optical power.

The tunable optical element 120 may also be a combination of any of the above elements in FIGS. 5A-5C such as, for example, a tunable lens with an SLM. Mechanically controlled telescopes, deformable adaptive mirrors, or other arrays of tunable optical elements can also be utilized for the functionality required by the tunable optical element 120.

Figure 6:
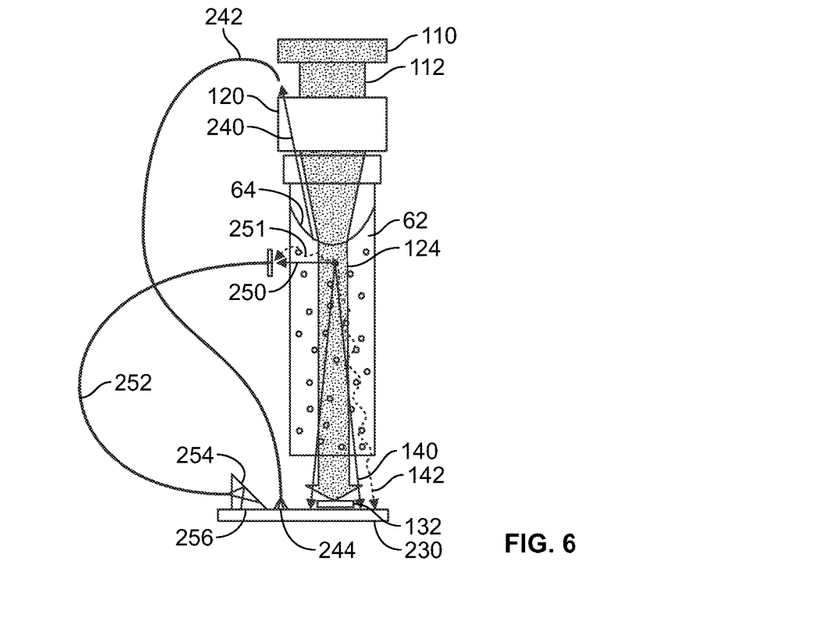
FIG. 6 is a schematic view of an alternative optical measurement system that takes multiple optical measurements on a single detector.

FIG. 6 illustrates an alternative system that can receive multiple optical measurements when an input beam is transmitted along the primary axis of a vial or well. Further, the system receives the multiple optical measurements on a single detector 230. The exemplary system in FIG. 6 is illustrative for implementation of various components used for multiple optical measurements, which can be combined in any other arrangements In FIG. 6, a back scatter signal 240 is collected by an optical fiber 242 near the free surface 64 of the liquid 62. The collection of the back scatter signal 240 may be facilitated by the addition of optical elements in front of the optical fiber 242 or by shaping the end facet of the optical fiber 242. The back scatter output signal 244 from the end of the fiber 242 is located at a physical position on the detector 230 that is unused for the measurement of the forward scatter signal 140 or the fluorescence signal 142.

In cases when optical access generally normal to the input beam direction is possible, a side scatter signal 250 and/or a side fluorescence signal 251 may be transmitted by a second optical fiber 252 to the detector 230. The optical fiber 252 is located near the vial's side surface and may collect the side scatter signal 250 and/or the side fluorescence signal 251 with additional coupling optics (as shown in FIG. 6), although additional coupling optics are not necessary. The output light 256 exiting the output end of the second optical fiber 252 is coupled to the detector 230 using a prism 254. Because the detector 230 must be located near the bottom surface of the well, the prism 254 allows the second optical fiber 252 to enter the detector region from the horizontal direction, thereby minimizing the height requirement for mechanical access to the detector 230. One or both sides of the prism 254 may contain a dielectric coating for rejection of the incident light wavelength, which can be useful in fluorescence measurements. The output signal(s) 256 from the side scatter signal 250 and the side fluorescence signal 251 can also be spatially separated via optics (like the prism 254) before being transmitted to the detector 230. The output signal(s) 256 from the side scatter signal 250 and/or a side fluorescence signal 251 are then sent to a second physical position(s) on the detector 230 not used for the forward scatter signal 140 or the fluorescence signal 142, which are transmitted past the beam dump 132. Accordingly, when side access is available to a vial, several types of optical measurements of the liquid 62 can be detected by the single detector 230 and the information can then be used to determine the types, amounts, and/or concentrations of the particles located within the liquid 62.

Figure 7:
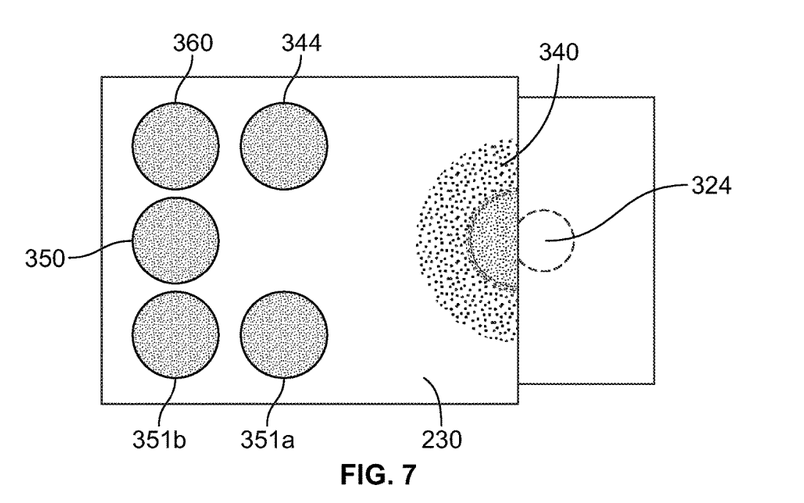
FIG. 7 illustrates an exemplary single detector for the system of FIG. 6 that can detect multiple types of signals.

FIG. 7 illustrates an exemplary layout of the detector 230 for multiple measurements from a liquid sample. The dashed circular line region 324 of the detector 230 represents a physical position of the blocked beam due to the beam dump 132. The forward scatter signal 140 is detected in a region 340 of the detector 230 that is located concentrically around the dashed circular line region 324. The various optical fibers (e.g., the optical fibers 242, 252 in FIG. 6) from the top and sides of the vial carry several complementary signals that are also detected by the same detector 230. For example, the back scatter signal 244 from the first optical fiber 242 can be detected at the top middle region 344 of the detector 230. The side scatter signal 250 can be measured at the left middle region 350. A first fluorescence signal can be detected at the lower middle region 351a (e.g., within a first wavelength band or at a different angle), while a second fluorescence signal can be detected at the lower left region 351b (e.g., within a second wavelength band or at a different angle) of the detector 230. An additional side scatter signal at a different angle can also be detected at the top left region 360 of the detector 230. Of course, more or less output signals can be detected by the detector 230. Furthermore, while FIG. 7 is provided for the purpose of illustrating multiple measurements on a single detector, only a single measurement (forward scatter signal 140 in FIG. 3) can be measured, as would be the case for the detector 130 when no forward fluorescence is to be detected.

Figure 8A:
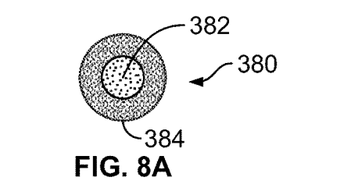
FIG. 8A illustrates a beam attenuation device in which only a central portion of the input beam is attenuated, so as to allow an outer portion of the beam to be measured for absorbance of the liquid sample.

FIG. 8A illustrates a beam attenuation device 380 that can be used instead of the beam dump 132 (FIGS. 3, 4, and 6). In the beam attenuation device 380, a central portion 382 of the incident beam that has traveled though the liquid 62 is attenuated, and the peripheral portion 384 is blocked, preferably by an opaque structure.

Figure 8B:
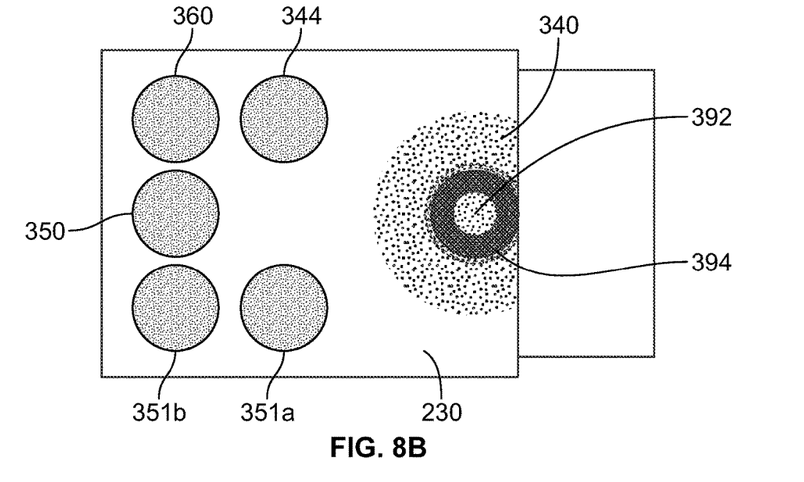
FIG. 8B illustrates the single detector of FIG. 7, whereby an absorbance measurement is also detected by use of the beam attenuation device of FIG. 8A.

In FIG. 8B, the beam attenuation device 380 allows for an absorbance measurement in the right middle region 392 of the detector 230. The peripheral region 394 on the detector 230 around the right middle region 392 has substantially no signal due to the preferably opaque peripheral portion 384 of the beam attenuation device 380. Because the forward scatter signal 140 (FIG. 6) is particularly useful at low particle concentrations or with weak scattering signals, simultaneous absorbance and scattering measurements are challenging because a wide dynamic range of the detector 230 is required. According to this aspect of the present invention, a part of the input beam is partially transmitted to the central region 392 of the detector 230 via the beam attenuation device 380, bringing it to intensities low enough that the same detector 230 can measure it simultaneously with the forward scatter signal 140. Using this alternative arrangement of FIGS. 8A and 8B, an absorbance measurement can also be carried out, enabling measurement of high particle concentrations. Furthermore, the present invention contemplates a system that uses both the beam dump 132 and the beam attenuation device 380 that are separately moved into and out of the path of the incident beam to allow the same detector 230 to provide the output detection patterns illustrated in both FIG. 7 and FIG. 8B.

Because it is advantageous to limit the number of back reflections that are detected by the detector 130, 230, the present invention also contemplates the use of an angled surface at the bottom of each well (as opposed to a horizontal surface) within the microplate, or the bottom surface of an individual vial. The angled surface helps to eliminate some of the back reflections that are incident upon the detector 130, 230. Furthermore, it is also advantageous to have the sidewalls of each of the wells be made of absorbing material (such as a black plastic) to absorb some of the retro-reflections. The bottom surface is preferably very thin, transmissive, and has a surface roughness below 10 nm.

It should be noted that the present invention has been described relative to a free surface of a liquid located within a liquid-containing well. However, the present invention is useful on one or more free surfaces, such as the free surface of a drop of a liquid sample that has a curved free surface or surfaces. Furthermore, while the sample-containing well has been described as being elongated, the well could also have a much more shallow shape. For example, the length of the well may have a dimension that is similar to its diameter.

Each of these embodiments and obvious variations thereof is contemplated as falling within the spirit and scope of the claimed invention, which is set forth in the following claims. Moreover, the present concepts expressly include any and all combinations and subcombinations of the preceding elements and aspects.

The invention claimed is:

1. An optical measurement system for measuring at least one characteristic of particles within a liquid that is contained in a well, comprising:
   a light source for transmitting an input beam toward a free surface of the liquid and generally parallel to a central axis of the well;
   a tunable optical element located between the light source and the free surface of the liquid, the tunable optical element for altering the shape of the input beam, wherein the tunable optical element is mechanically or electrically adjustable to alter the shape of the input beam between a first shape resulting in the input beam not being collimated and a second shape resulting in collimating the input beam during the operation of the optical measurement system to compensate for a distortion determined by the optical characteristics of the free surface of the liquid;
   a detector located below the well for receiving a forward scatter signal indicative of at least one characteristic of the particles within the liquid and for detecting the optical characteristics of the free surface of the liquid; and
   an input-beam attenuator to inhibit a transmitted portion of the input beam from impinging upon the detector, the transmitted portion of the input beam being the portion of the input beam that has transmitted through the liquid.

2. The optical measurement system of claim 1, wherein the input-beam attenuator is a beam block located adjacent to the detector and below a bottom surface of the well.

3. The optical measurement system of claim 1, wherein the input beam causes a fluorescence signal to be emitted from the particles, the detector further receiving a fluorescence signal indicative of at least one characteristic of the particles within the liquid.

4. The optical measurement system of claim 1, wherein the particles include bacteria and the at least one characteristic indicated by the forward scatter signal is the amount of bacteria within the liquid.

5. The optical measurement system of claim 1, further including at least one optical fiber to gather additional signals related to particle characteristics from a side or a top of the well, the optical fibers providing the additional signals to the detector.

6. The optical measurement system of claim 1, further including a controller coupled to the tunable optical element, the controller for tuning optical parameters associated with the tunable optical element so as to alter the shape of the input beam.

7. The optical measurement system of claim 6, wherein the controller receives information from the detector for tuning the optical parameters so as to properly compensate for the distortion associated with the free surface.

8. The optical measurement system of claim 7, wherein the tuned optical parameters cause the transmitted portion of the input beam within the liquid in the well to be substantially collimated or focused.

9. The optical measurement system of claim 6, wherein the controller receives information associated with the free surface of the liquid for tuning the optical parameters so as to properly compensate for the distortion associated with the free surface.

10. The optical measurement system of claim 1, wherein the tunable optical element causes the shape of the transmitted portion of the input beam within the liquid to be substantially collimated or focused.

11. The optical measurement system of claim 1, wherein the tunable optical element is at least one of a group consisting of an adjustable lens, a lens that is shaped electronically or mechanically, and a spatial light modulator.

12. The optical measurement system of claim 1, wherein the well is an elongated interior well within a microplate having a plurality of wells that are positioned in a two-dimensional arrangement.

13. The optical measurement system of claim 1, wherein the tunable optical element includes a first optical element, a second optical element and an actuator to impart a force on a structure to adjust the distance between the first and second optical elements.

14. A method of determining at least one characteristic of particles within a liquid that is contained in a well, comprising:
    transmitting a light beam toward a free surface of the liquid;
    detecting the optical characteristics of the free surface of the liquid;
    determining a distortion of the free surface of the liquid based on the detected optical characteristics;
    altering a shape of the light beam between a first shape resulting in the input beam not being collimated and a second shape resulting in collimating the input beam to result in a substantially focused beam shape within the liquid to compensate for the distortion determined by the optical characteristics of the free surface of the liquid after the input beam has been subjected to optical distortions at the free surface, the altering being performed by a tunable optical element between the light beam and the free surface of the liquid, wherein the tunable optical element is mechanically or electrically adjustable to alter the shape of the light beam between the first and second shape;
    attenuating the input beam at a location before a detector; and
    receiving forward scatter signals at the detector, the forward scatter signals being indicative of at least one characteristic of the particles.

15. The method of claim 14, wherein the forward scatter signals are located nearer to a wall of the well relative to the input beam with the substantially focused beam shape.

16. The method of claim 14, wherein the tunable optical element alters the shape of the light beam to a substantially collimated or focused beam shape in response to feedback from the detector.

17. The method of claim 14, further including receiving additional signals indicative of at least one characteristic of particles, the additional signals coming from a location at a side of the well or a top of the well, the additional signals being transmitted via an optical fiber.

18. An optical measurement system for measuring a liquid sample within a well, comprising:
    a light source configured to transmit light through the liquid sample within the well;
    a detector configured to measure optical signals derived from the transmitted light within the liquid sample and to detect the optical characteristics of the free surface of the liquid; and
    a tunable optical element positioned between the light source and the well, the tunable optical element mechanically or electrically adjustable to adjust the shape of the input beam between a first shape resulting in the input beam not being collimated and a second shape resulting in collimating the input beam to shape the light to compensate for distortions induced by a surface of the liquid sample, the distortions determined by the optical characteristics of the free surface of the liquid, the adjustment occurring during the operation of the optical measurement system.

19. The optical measurement system of claim 18, wherein the tunable optical element comprises a tunable lens with an adjustable curvature coupled to an electrical circuit that controls the curvature of the tunable lens.

* * * * *